United States Patent [19]

Kato et al.

[11] Patent Number: 5,039,972

[45] Date of Patent: Aug. 13, 1991

[54] OXYGEN SENSOR

[75] Inventors: Nobuhide Kato, Ama; Masanori Katsu, Nagoya, both of Japan

[73] Assignee: NGK Insulators, Ltd., Aichi, Japan

[21] Appl. No.: 522,837

[22] Filed: May 14, 1990

[30] Foreign Application Priority Data

May 15, 1989 [JP] Japan .................. 1-55572[U]

[51] Int. Cl.$^5$ ............................ H01C 7/00
[52] U.S. Cl. ............................ 338/34; 73/31.05
[58] Field of Search .................. 338/34; 204/425, 426, 204/427, 428, 412, 431, 432; 73/25.03, 23.31, 31.05, 23.2; 422/98

[56] References Cited

U.S. PATENT DOCUMENTS

| | | | |
|---|---|---|---|
| 3,959,764 | 5/1976 | Allman | 338/34 |
| 3,959,765 | 5/1976 | Stewart | 338/34 |
| 4,377,801 | 3/1983 | Weber et al. | 338/34 |
| 4,401,967 | 8/1983 | Miwa et al. | 338/34 |
| 4,417,228 | 11/1983 | Takami et al. | 338/34 |
| 4,733,056 | 3/1988 | Kojima et al. | 219/543 |
| 4,818,363 | 4/1989 | Bayha et al. | 204/426 |
| 4,943,330 | 7/1990 | Iino et al. | 204/426 X |
| 4,958,514 | 9/1990 | Takami et al. | 73/25.03 |

Primary Examiner—Marvin M. Lateef
Attorney, Agent, or Firm—Parkhurst, Wendel & Rossi

[57] ABSTRACT

An oxygen sensor has a planar sensor element which generates electromotive forces or varies an electric resistance between electrodes formed on opposite surfaces of the planar sensor element depending upon concentrations of oxygen in exhaust gases, a metallic housing member for housing the sensor element therein, a ceramic powder placed around the planar sensor element in the metallic housing member and adapted to fix the planar sensor element and form a gas-sealed section and ceramic supporters for compacting the ceramic powder under a given pressure therebetween. The portion of at least one of the ceramic supporters which contacts the ceramic powder is provided with a projection.

2 Claims, 5 Drawing Sheets

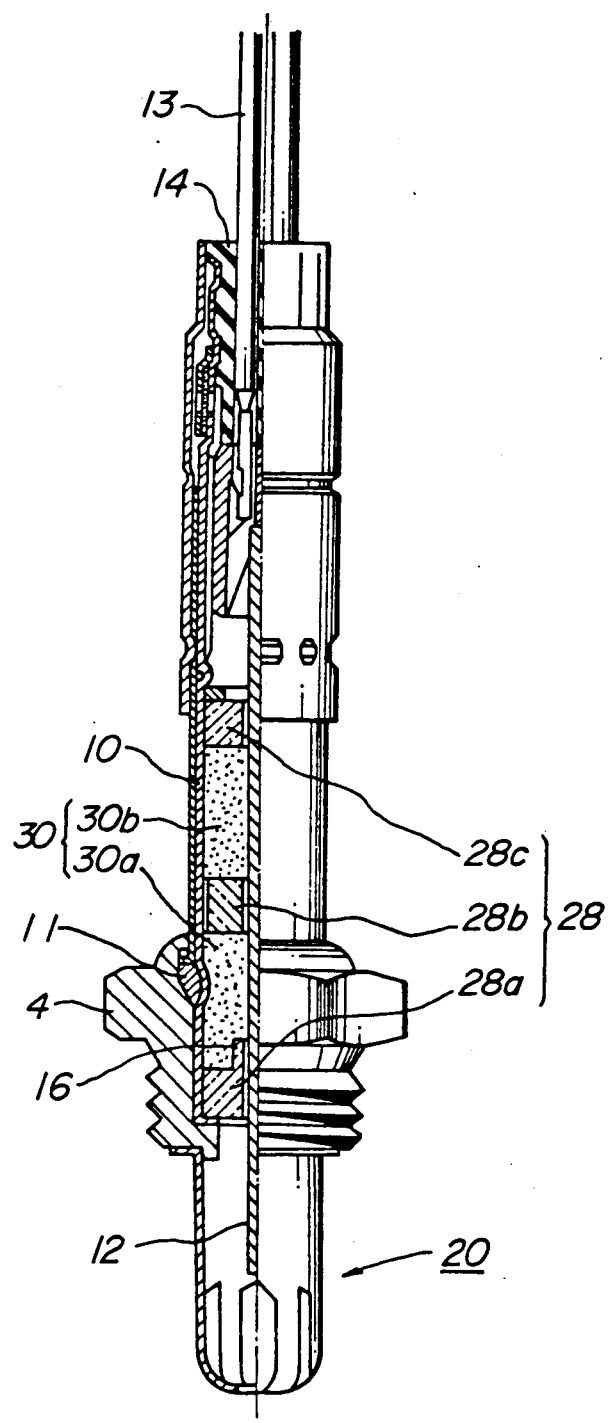
FIG_1a
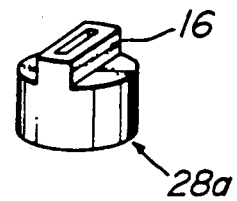
FIG_1b

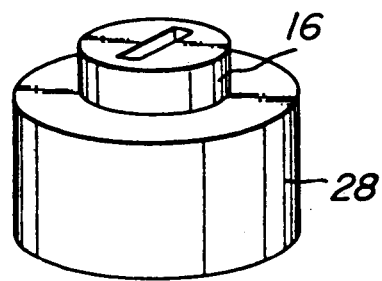
FIG_4a
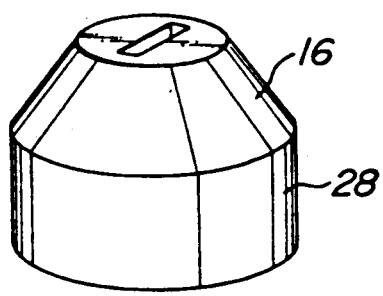
FIG_4b
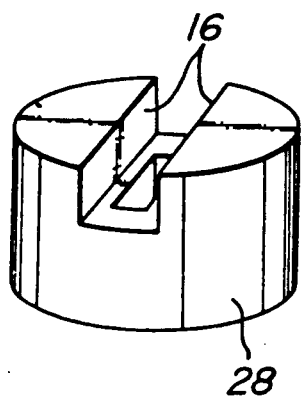
FIG_4c

OXYGEN SENSOR

BACKGROUND OF THE INVENTION

1. Field of the Invention

The present invention relates to improvement on oxygen sensors, which each comprise a planar sensor element capable of generating electromotive forces between electrodes or capable of varying an electric resistance between them depending upon the concentration of oxygen in exhaust gases, a metallic housing member for housing the sensor element, a ceramic powder placed in the metallic housing member and adapted for fixing the planar oxygen sensor element and forming a gas-sealed section, and ceramic supporters for compacting the ceramic powder under a given pressure.

2. Related Art Statement

As shown in FIG. 5a, a ceramic powder 30 such as talc is filled between a metallic cap 10 and a sensor element 12, the sensor element 12 is fixed by compacting the ceramic powder under pressure, and air is used as a reference oxygen atmosphere. In such an oxygen sensor, the air as the reference oxygen atmosphere is isolated, by means of the compacted ceramic powder 30, from a gas to be measured.

Ceramic supporters 28: 28a, 28b and 28c are used for forming the gas-sealed section by compacting the ceramic powder such as talc under pressure, and as shown in a perspective view of FIG. 5b by way of example, that portion of each of the ceramic supporters which contacts the ceramic powder 30 such as talc is flat.

However, in the oxygen sensor of this construction, when the sensor undergoes heating, a gap is formed between the lower end surface of the ceramic supporter 28a and the cap 10 and/or between the upper end surface of the ceramic supporter 28a and the talc 30a, due to difference in thermal expansion between the cap 10 and the ceramic supporter 28a. At that time, when vibrations are applied to the sensor, the ceramic supporter 28a vibrates to vibrate the sensor element 12. As a result, the sensor element is vibrated, and fixing forces and the gas-tightness between the sensor element and the talc are deteriorated.

SUMMARY OF THE INVENTION

It is an object of the present invention to solve the above-mentioned problems, and to provide an oxygen sensor which will not cause loosening of talc even during long time use, that is, which will not deteriorate the fixing forces of the sensor element and the gas-tightness of the gas-sealed section.

The oxygen sensor according to the present invention comprises a planar sensor element adapted to generate electromotive forces between electrodes or adapted to vary electric resistance between them depending upon concentrations of oxygen in exhaust gases, a metallic housing member housing the sensor element, a ceramic powder placed around the planar sensor element in the metallic housing member and adapted to fix the planar sensor element and form a gas-sealed section, and ceramic supporters placed in the metallic housing member and adapted for compacting a ceramic powder under a given pressure, this ceramic powder being to fix the planar sensor element and form the gas-sealed section, wherein a projection is provided on that portion of at least one of the ceramic supporters which contacts the ceramic powder.

In the above construction, since the projection is provided on that portion of the ceramic supporter which contacts the ceramic powder, the projection is radially pressed with the ceramic powder. Therefore even when vibrations and/or heat cycling are applied to the oxygen sensor, the ceramic supporter will not vibrate relative to the oxygen sensor, so that the sensor element is not vibrated. Accordingly, almost no loosing of the ceramic powder occurs. That is, deterioration in the fixing forces of the sensor element and the gas-tightness of the gas-sealed section is extremely decreased.

Although a plurality of the ceramic supporters are provided, the above function of the invention can be exhibited by providing at least one of the ceramic supporters with the projection. The greater the number of the ceramic supporters on which the projection is provided, the smaller the deterioration in the fixing forces and the gas-tightness. Needless to say, the maximum effect can be obtained when all the ceramic supporters are provided with the projections.

These and other objects, features and advantages of the invention will be appreciated upon reading of the following description of the invention when taken in conjunction with the attached drawings, with the understanding that some modifications, variations and changes of the same could be made by the skilled person in the art to which the invention pertains without departing from the spirit of the invention or the scope of claims appended hereto.

BRIEF DESCRIPTION OF THE DRAWINGS

For a better understanding of the invention, reference is made to the attached drawings, wherein:

FIGS. 1a and 1b are a partial sectional view of a structural example of an oxygen sensor according to the present invention and a perspective view of a ceramic supporter thereof, respectively;

FIGS. 4a through 4c are perspective views of other ceramic supporters according to the present invention.

DETAILED DESCRIPTION OF THE INVENTION

Figure 2:
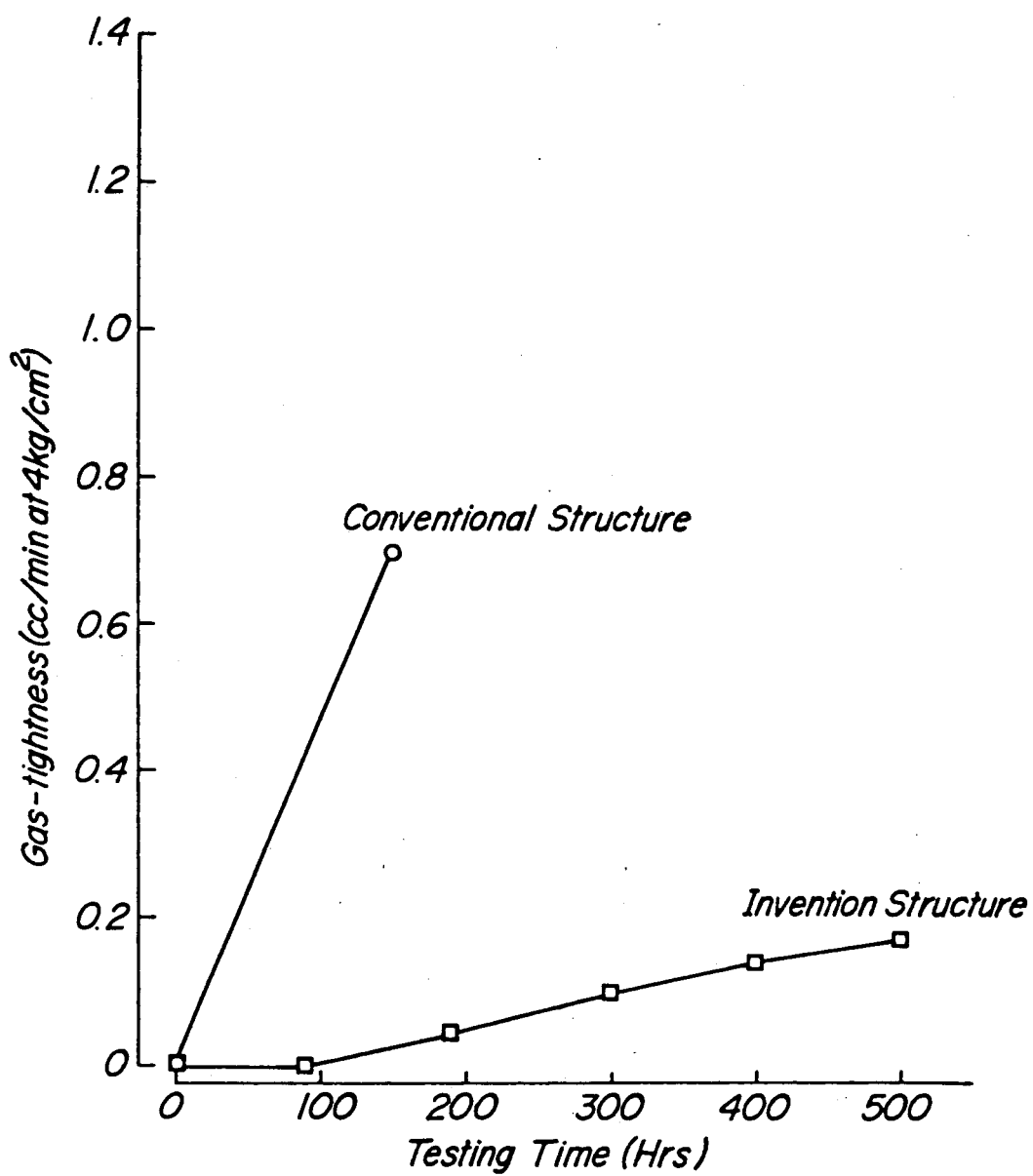
FIG. 2 is a graph showing the relationship between gas-tightness and testing time under vibrating-heating cycle conditions.

FIGS. 1a and 1b are the partial sectional view of one structural example according to the present invention and the perspective view of the ceramic supporter, respectively. In the oxygen sensor 20 according to the present invention shown in FIGS. 1a and 1b, a planar sensor element 12 is fixed in a cylindrical metallic cap 10 through talc 30: 30a and 30b filled between ceramic supporters 28: 28a, 28b and 28c. The talc 30: 30a and 30b forms the gas-sealed sections. In this oxygen sensor, as shown in FIG. 1b, a projection 16 is formed on that portion of the ceramic supporter 28a which contacts talc, and the sensor element is passed through a central portion of the projection. The sensor element 12 is fixed with talc 30 through compacting the talc 30 by means of the ceramic supporters 28 under given pressure.

On the other hand, a rubber plug 14 is fixed, by caulking the cap 10, to an upper open end side opposed to the side on which the cap 10 is fixed to the housing 4 through a gas-tight ring 11. Lead wires 13 are inserted through the rubber plug 14. Thereby, the cap 10 is sealed. Ends of the lead wires 13 are electrically connected to terminal electrodes of the oxygen sensor 12.

When the thus constituted oxygen sensor 20 undergoes heat, a gap is formed between the lower end face of the ceramic supporter 28a and the cap 10 due to difference in thermal expansion between the cap 10 and the ceramic supporter 28a. However, since the projection 16 of the ceramic supporter 28a is fixed with talc 30a while being pressed radially with talc 30a, the ceramic supporter 28a will not vibrate relative to the oxygen sensor 20 and the sensor element 12 is not vibrated, even if the oxygen sensor receives vibrations. Accordingly, almost no deterioration in the fixing forces and gas-tightness between the sensor element and the talc due to vibrations of the sensor element 12 will occur.

With respect to the conventional structure oxygen sensor and the oxygen sensor according to the present invention, deterioration in the gas-tightness of talc was examined in vibration-heat cycling test, and results are shown in FIG. 2. The vibration-heat cycling conditions were that a vibration frequency and a vibration acceleration were 50–250 Hz (swept from 50 to 250 Hz in 30 minutes) and 30–50 G, respectively, while the heat cycling was repeatedly effected between 900° C. for 30 minutes and room temperature for 25 minutes. The gas-tightness of talc was examined by measuring an amount of air compressed at 4 kg/cm² passing through both the talc sections 30a and 30b. As is clear from FIG. 2, deterioration in the gas-tightness of talc due to vibrations and heat cycling of the oxygen sensor can remarkably be decreased by employing the structure in which the ceramic supporter is provided with the projection as in the present invention.

Figure 3:
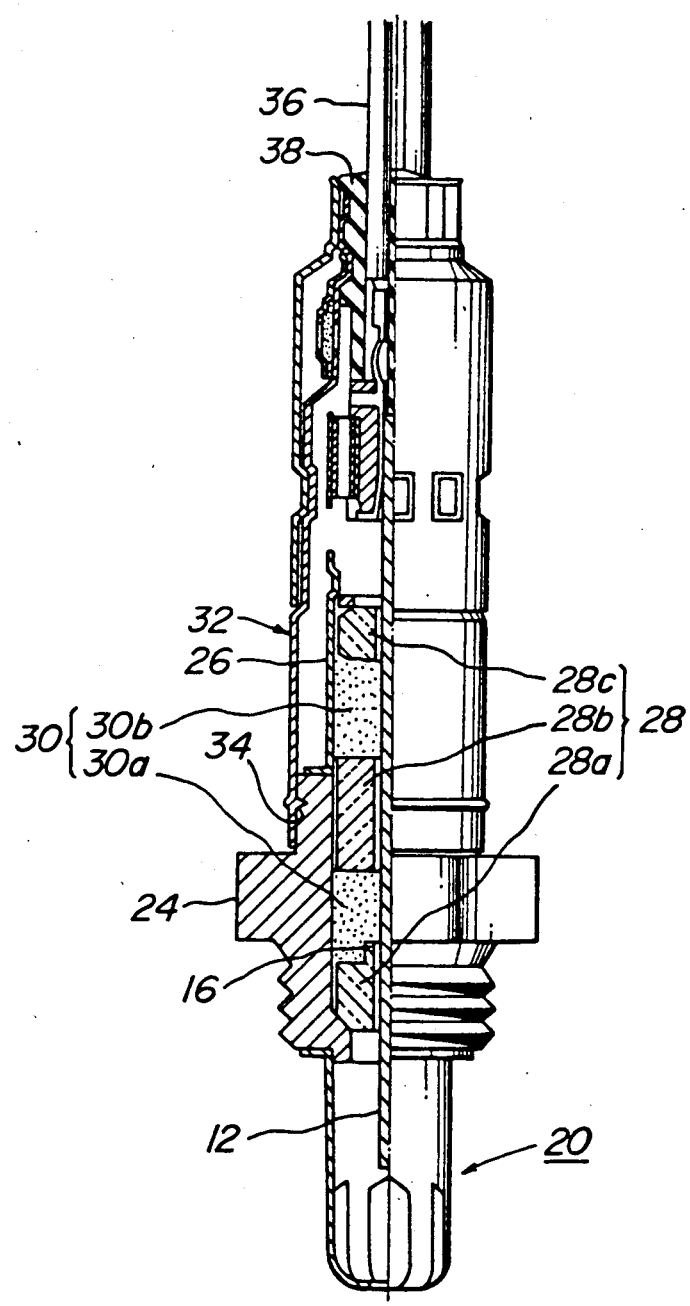
FIG. 3 is a partial sectional view of another structural example according to the present invention.
Figure 5A:
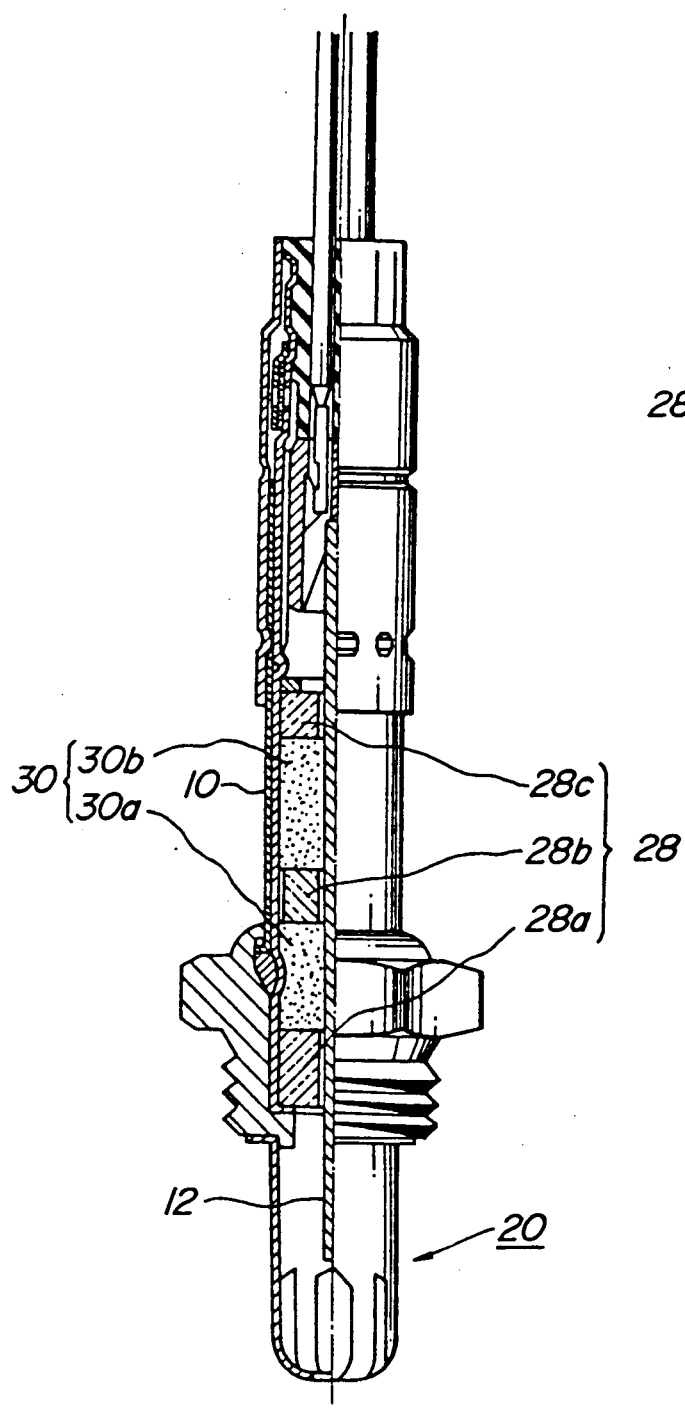
FIGS 5a and 5b show a structural example of the conventional oxygen sensor.
Figure 5B:
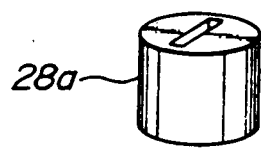

FIG. 3 is a partially sectional view of another embodiment according to the present invention. In the oxygen sensor 20 according to the present invention shown in FIG. 3, a planar sensor element 12 is fixed in a metallic housing member 24 and a cylindrical metallic inner cylinder 26 with talc 30: 30a and 30b filled between ceramic supporters 28: 28a, 28b and 28c. The talc 30: 30a and 30b forms the gas-sealed sections. The metallic inner cylinder is fixed to the housing by welding. As similarly with the above-mentioned embodiment, a projection 16 is provided on the ceramic supporter 28a. In order to protect the sensor element 12 from the exterior environment, a metallic outer cylinder 32 is fitted to the outer peripheral portion of an upper annular groove or indentation 34 of the housing member 24, and the former is gas-tightly fixed to the entire outer periphery of the latter by welding. On the other hand, a rubber plug 38 is sealingly fixed to an upper open end side of the outer cylinder 32 which is opposed to the side of the outer cylinder 32 fitted to the housing member 24. Lead wires 36 are inserted through the rubber plug 38. The lead wires 36 are electrically connected to terminal electrodes of the sensor element 12 at their ends, respectively. The embodiment in FIG. 3 differs from that in FIG. 1 in that the lower end face of the ceramic supporter 28a contacts the metallic housing member 24.

The present invention is not limited to the above-mentioned embodiments, but various modifications and variations can be made. For example, although only that portion of the ceramic supporter 28a which contacts the talc 30a is provided with the projection 16, it goes without saying that that portion of the other ceramic supporter or supporters which contacts the talc may be provided with such a projection. The projection provided on the ceramic supporter is not limited to that shown in FIG. 1b, and it may be any of those shaped as shown in FIGS. 4a through 4c. That is, it is possible to use a projection 16 concentric with the ceramic supporter 28 as shown in FIG. 4a, a tapered projection 16 shown in FIG. 4b, or opposed projections 16 formed by providing a recess to surround the central sensor element as shown in FIG. 4c.

Further, in the above embodiments, although the planar sensor element is used in the above embodiments, needless to say, a cylindrical sensor element may be used.

As is clear from the above-mentioned explanation, according to the oxygen sensor of the present invention, since at least one of the ceramic supporters defining the gas-tightly sealed section is provided with the projection, the projection can radially be pressed through the ceramic powder, so that even when vibrations and/or heat cyclings are applied to the oxygen sensor, almost no loosening of the ceramic powder occurs. Consequently, the oxygen sensor will be free from deterioration in the fixing forces of the oxygen sensor element and the gas-tightness of the gas-sealed section.

What is claimed is:

1. An oxygen sensor comprising a planar sensor element which generates electromotive forces or varies an electric resistance between electrodes formed on opposite surfaces of the planar sensor element depending upon concentrations of oxygen in exhaust gases, a metallic housing member for housing the sensor element therein, a ceramic powder placed around the planar sensor element in the metallic housing member and adapted to fix the planar sensor element and form a gas-sealed section and ceramic supporters for compacting the ceramic powder under a given pressure therebetween, wherein that portion of at least one of the ceramic supporters which contacts the ceramic powder is provided with at least one projection, said at least one projection projecting into said ceramic powder.

2. The oxygen sensor according to claim 1, wherein the ceramic supporters each have an annular shape, a through hole is provided at a central portion of each of the ceramic supporters for allowing passing of the sensor element therethrough, and the projection is formed around the through hole to surround the sensor element.

* * * * *